(12) United States Patent
Cauley et al.

(10) Patent No.: US 10,310,042 B2
(45) Date of Patent: Jun. 4, 2019

(54) HIERRARCHICAL MAPPING FRAMEWORK FOR COIL COMPRESSION IN MAGNETIC RESONANCE IMAGE RECONSTRUCTION

(71) Applicant: THE GENERAL HOSPITAL CORPORATION, Boston, MA (US)

(72) Inventors: Stephen Cauley, Cambridge, MA (US); Jonathan Polimeni, Cambridge, MA (US); Kawin Setsompop, Cambridge, MA (US); Lawrence Wald, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 138 days.

(21) Appl. No.: 15/305,436

(22) PCT Filed: Apr. 23, 2015

(86) PCT No.: PCT/US2015/027297
§ 371 (c)(1),
(2) Date: Oct. 20, 2016

(87) PCT Pub. No.: WO2015/164606
PCT Pub. Date: Oct. 29, 2015

(65) Prior Publication Data
US 2017/0045599 A1    Feb. 16, 2017

Related U.S. Application Data

(60) Provisional application No. 61/983,690, filed on Apr. 24, 2014.

(51) Int. Cl.
*G01R 33/561* (2006.01)
*G01R 33/56* (2006.01)
(Continued)

(52) U.S. Cl.
CPC ....... *G01R 33/5612* (2013.01); *G01R 33/482* (2013.01); *G01R 33/4824* (2013.01);
(Continued)

(58) Field of Classification Search
CPC .............. G01R 33/5612; G01R 33/482; G01R 33/4824; G01R 33/5608; G01R 33/5611;
(Continued)

(56) References Cited

U.S. PATENT DOCUMENTS

2006/0208731 A1   9/2006   Wang et al.
2010/0013472 A1   1/2010   Buehrer et al.
(Continued)

OTHER PUBLICATIONS

Cauley, et al., A General Hierarchical Mapping Framework (HMF) for Coil Compression, Proc. Intl. Soc. Mag. Reson. Med., 2014, 22:4393.
(Continued)

*Primary Examiner* — Rodney A Bonnette
(74) *Attorney, Agent, or Firm* — Quarles & Brady LLP

(57) ABSTRACT

Systems and methods for a hierarchical mapping framework ("HMF"} for coil compression are provided. The HMF-based coil compression can be applied to existing coil compression algorithms to improve their performance. The receive channels associated with a coil array are divided into subgroups based on the strength of their mutual correlation. In each subgroup, one or more virtual channels are produced based on the channels not in the subgroup. The virtual channels are produced using a coil compression algorithm subject to a hierarchically semiseparable channel mixing across the subgroups. Images are reconstructed for the subgroups and then combined to produce the final image of the subject.

8 Claims, 3 Drawing Sheets

(51) Int. Cl.
  *G01R 33/48*     (2006.01)
  *G01R 33/36*     (2006.01)
  *A61B 5/00*      (2006.01)
  *A61B 5/055*     (2006.01)

(52) U.S. Cl.
  CPC ...... *G01R 33/5608* (2013.01); *G01R 33/5611* (2013.01); *A61B 5/055* (2013.01); *A61B 5/7246* (2013.01); *A61B 5/7285* (2013.01); *G01R 33/3664* (2013.01)

(58) Field of Classification Search
  CPC .. G01R 33/3664; A61B 5/7246; A61B 5/7285
  See application file for complete search history.

(56) References Cited

U.S. PATENT DOCUMENTS

| | | |
|---|---|---|
| 2011/0006766 A1 | 1/2011 | Jurrissen et al. |
| 2013/0099786 A1 | 4/2013 | Huang et al. |
| 2013/0134975 A1 | 5/2013 | Nehrke et al. |
| 2014/0070804 A1 | 3/2014 | Huang et al. |

OTHER PUBLICATIONS

Cauley, et al., Fast Reconstruction for Multichannel Compressed Sensing Using a Hierarchically Semiseparable Solver, Magnetic Resonance in Medicine, 2015, 73:1034-1040.

Zhang, et al., Coil Compression for Accelerated Imaging with Cartesian Sampling, Magnetic Resonance in Medicine, 2013, 69(2):571-582.

PCT International Search Report and Written Opinion, PCT/US2015/027297, dated Jul. 15, 2015.

HIERRARCHICAL MAPPING FRAMEWORK FOR COIL COMPRESSION IN MAGNETIC RESONANCE IMAGE RECONSTRUCTION

CROSS-REFERENCE TO RELATED APPLICATIONS

This application represents the U.S. National Stage of International Application No. PCT/US2015/027297, filed on Apr. 23, 2015 which claims the benefit of U.S. Provisional Patent Application Ser. No. 61/983,690, filed on Apr. 24, 2014, both of which are incorporated herein by reference for all purposes.

STATEMENT REGARDING FEDERALLY SPONSORED RESEARCH

This invention was made with government support under EB012107 and MH093765 awarded by the National Institutes of Health. The government has certain rights in the invention.

BACKGROUND OF THE INVENTION

The field of the invention is systems and methods for magnetic resonance imaging ("MRI"). More particularly, the invention relates to systems and method for accelerated MRI and parallel imaging, including simultaneous multislice imaging ("SMS").

MRI scans can often times be lengthy and, thus, not feasible for clinical application. These otherwise lengthy scans can have their scan time significantly reduced by implementing parallel imaging ("PI") techniques to accelerate the data acquisition process. The data acquisition process is typically accelerated by undersampling k-space, such as by skipping phase-encoding or partition-encoding lines.

Typically, PI techniques make use of an array of radio frequency ("RF") receiver coils. Each coil in the array has a unique spatial sensitivity profile, which can be utilized to supplement the spatial encoding of magnetic resonance signals and to remove aliasing artifacts caused by undersampling k-space.

There is a growing trend towards using large coil arrays with PI techniques because larger coil arrays allow greater acceleration of the data acquisition while also increasing the attainable signal-to-noise ratio. These larger coil array are not without their drawbacks, however. For instance, the computational cost of many PI algorithms scales with the square of the number of channels in the coil array, thereby leading to long reconstruction times when larger coil arrays are used. This increase in reconstruction time creates a strong incentive to reduce the effective number of channels used for PI.

Coil compression techniques can be used to reduce the computation burden of working with larger coil arrays. In general, both hardware coil compression and software-based coil compression can be used to linearly combine the data acquired on multiple coils into a reduced number of virtual coils.

Several techniques for software-based coil compression have been developed so far, with most algorithms being configured for use with two-dimensional Cartesian acquisitions, the geometric-decomposition coil compression ("GCC") method recently proposed by T. Zhang, et al., in "Coil Compression for Accelerated Imaging with Cartesian Sampling," *Magn Reson Med,* 2013; 69(2):571-582. Other methods can be implemented for a wider range of sampling patterns. For example, global mapping methods, such as SVD compression, are applicable to a wide range of k-space sampling patterns. These global mapping methods suffer from low SNR retention at high coil compression rate, however.

In light of the foregoing, there remains a need for a coil compression technique that can be widely applied to different sampling patterns (e.g., both Cartesian and non-Cartesian sampling) without loss of SNR at high coil compression rates.

SUMMARY OF THE INVENTION

The present invention overcomes the aforementioned drawbacks by providing a method for reconstructing an image of a subject using a magnetic resonance imaging ("MRI") system and a hierarchical mapping framework ("HMF") based coil compression. Data is acquired from a subject using the MRI system, wherein the data is acquired using a plurality of receive channels associated with a radio frequency ("RF") coil array. The strength of correlation between the plurality of receive channels is determined and used to create subgroups of the receive channels, each subgroup being based on the determined strength of correlation between the plurality of receive channels. At least one virtual channel is produced for each subgroup using a hierarchical semiseparable channel mixing across the subgroups. An image is then reconstructed for each subgroup from the acquired data and using the receive channels and virtual channels in each respective subgroup. An image of the subject is then produced by combining the reconstructed images for each subgroup.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for a hierarchical mapping framework ("HMF") for coil compression that improves upon previously proposed coil compression algorithms. The proposed HMF can be applied to existing coil compression algorithms, such as GCC or SVD coil compression, to reconstruct images from data acquired using a highly-accelerated acquisition, such as a simultaneous multislice ("SMS") echo-planar imaging acquisition. For instance, using the HMF, the performance of SVD compression can be significantly improved. The application of HMF to SVD compression can therefore extend the benefits seen with GCC for Cartesian acquisitions to non-Cartesian acquisitions, with which GCC is incompatible.

Figure 1:
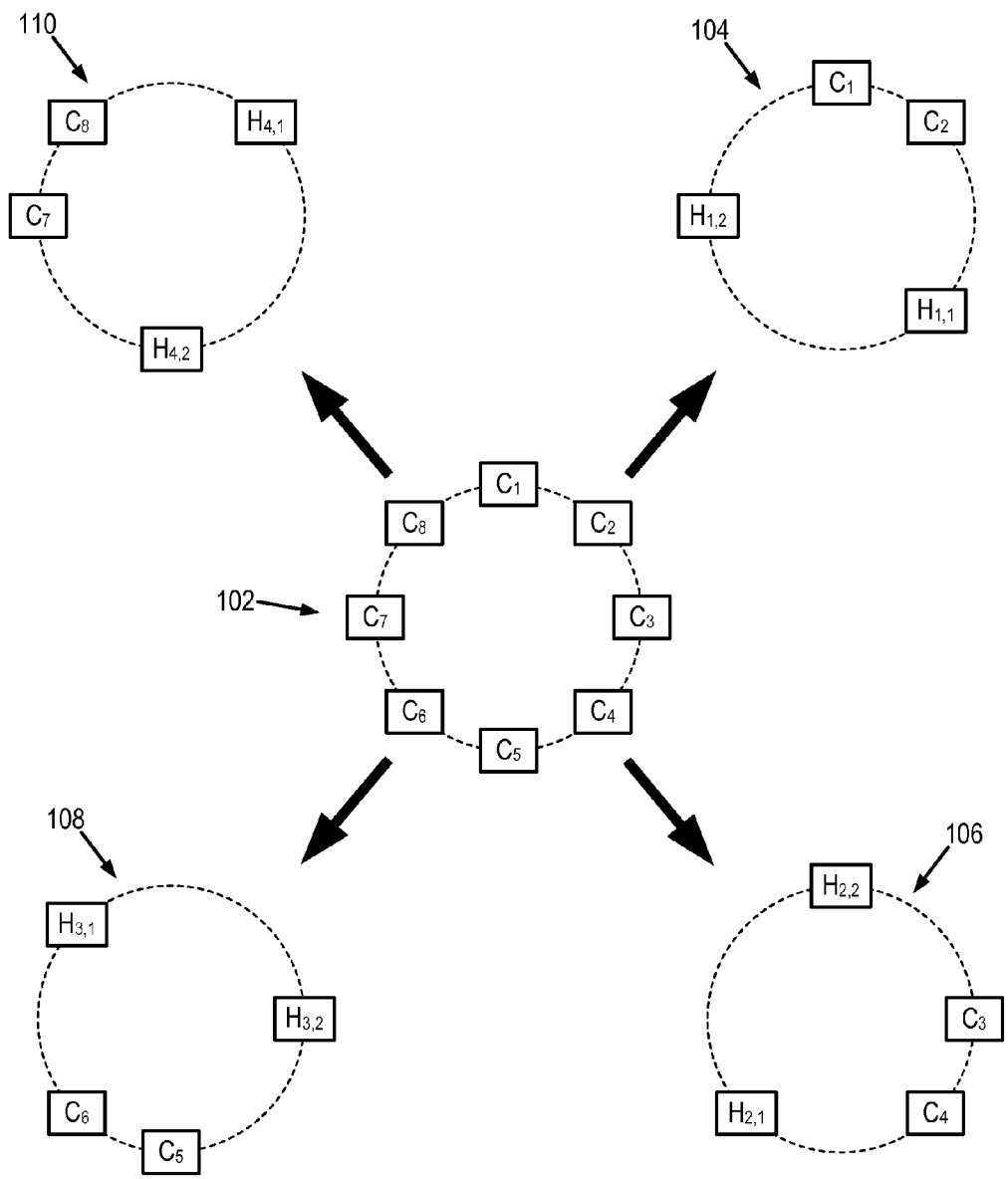
FIG. 1 is a schematic illustration of using a hierarchical mapping framework ("HMF") to create four subgroups of receive channels for a coil array that has eight receive channels.

The hierarchical mapping framework for coil compression mitigates the loss in signal typically associated with global compression. In HMF, channels are initially organized based on strength of correlation and are then divided into subgroups. Each subgroup has an associated set of virtual channels that will be used to capture contributions from those channels which are excluded from that particular subgroup. This process is schematically illustrated in FIG. 1, where a full set 102 of receive channels is divided into four subgroups 104, 106, 108, 110 each having a reduced number of channels. For example, the full set 102 includes eight channels, $\{C_n\}$ for n=1, . . . , 8. Subgroup 104 contains channels $\{C_1,C_2\}$ and two virtual channels, $\{H_{1,1},H_{1,2}\}$. The virtual channels, $\{H_{1,2},H_{2,2}\}$, are produced using a coil compression of the channels not included in subgroup 102. Likewise, subgroup 106 contains channels $\{C_3,C_4\}$ and two virtual channels $\{H_{2,1},H_{2,2}\}$; subgroup 108 contains channels $\{C_5,C_6\}$ and two virtual channels $\{H_{3,1},H_{3,2}\}$; and subgroup 110 contains channels $\{C_7,C_8\}$ and two virtual channels $\{H_{4,1},H_{4,2}\}$.

In order to efficiently model virtual channels for all subgroups, a hierarchal relationship is assigned across the subgroups. As one example, a hierarchically semiseparable ("HSS") channel mixing matrix, such as the following, can be utilized:

$$M = \begin{pmatrix} \begin{pmatrix} D_{2;1} & U_{2;1}B_{2;1,2}V_{2;2}^H \\ U_{2;2}B_{2;2,1}V_{2;1}^H & D_{2;2} \end{pmatrix} & \begin{pmatrix} U_{2;1} & R_{2;1} \\ U_{2;2} & R_{2;2} \end{pmatrix} B_{1;1,2}( W_{2;3}^H V_{2;3}^H \quad W_{2;4}^H V_{2;4}^H ) \\ \begin{pmatrix} U_{2;3} & R_{2;3} \\ U_{2;4} & R_{2;4} \end{pmatrix} B_{1;2,1}( W_{2;1}^H V_{2;1}^H \quad W_{2;2}^H V_{2;2}^H ) & \begin{pmatrix} D_{2;3} & U_{2;3}B_{2;3,4}V_{2;4}^H \\ U_{2;4}B_{2;4,3}V_{2;3}^H & D_{2;4} \end{pmatrix} \end{pmatrix}. \quad (1)$$

Here, the basis parameters $\{U,V\}$ can be generated using any linear channel compression technique, such as GCC or SVD coil compression, and $\{D\}$ represents the mixing matrix for each subgroup. The parameters $\{B,R,W\}$ allow for efficient propagation of the basis parameters $\{U,V\}$ to produce the virtual channels for each of the subgroups. With comparable compression factors, the HSS mixing matrix, M, allows for the same computational complexity as a global compression operation, but with improved reconstruction.

Based on PI reconstruction models such GRAPPA and slice-GRAPPA, the subgroups (and the associated virtual channels) can be used to produce the original PI channels. To further improve efficiency, pseudo-channels can be assigned to each subgroup to capture the dominant features. This is accompanied by solving a non-linear least squares problem to create pseudo-channels whose magnitude is the sum-of-squares combination of the original channels in each subgroup.

As an example to demonstrate the efficiency of the HMF method, consider a split slice-GRAPPA ("Sp-SG") formulation for SMS-EPI reconstruction of 2 mm isotropic voxels with a highly accelerated (e.g., MB=8) simultaneous multislice acquisition. In the example, the global SVD-based compression from 64 receive channels to 16 effective channels only retains 87% of the SNR. Using the HMF of the present invention, however, subgroups of size 8 can be formed with 8 virtual channels assigned to each subgroup. Assigning 2 pseudo-channels per group, the HMF method will also have 16 effective channels. This HMF strategy retains 99% of the SNR with the same computational complexity as the global compression.

Figure 2:
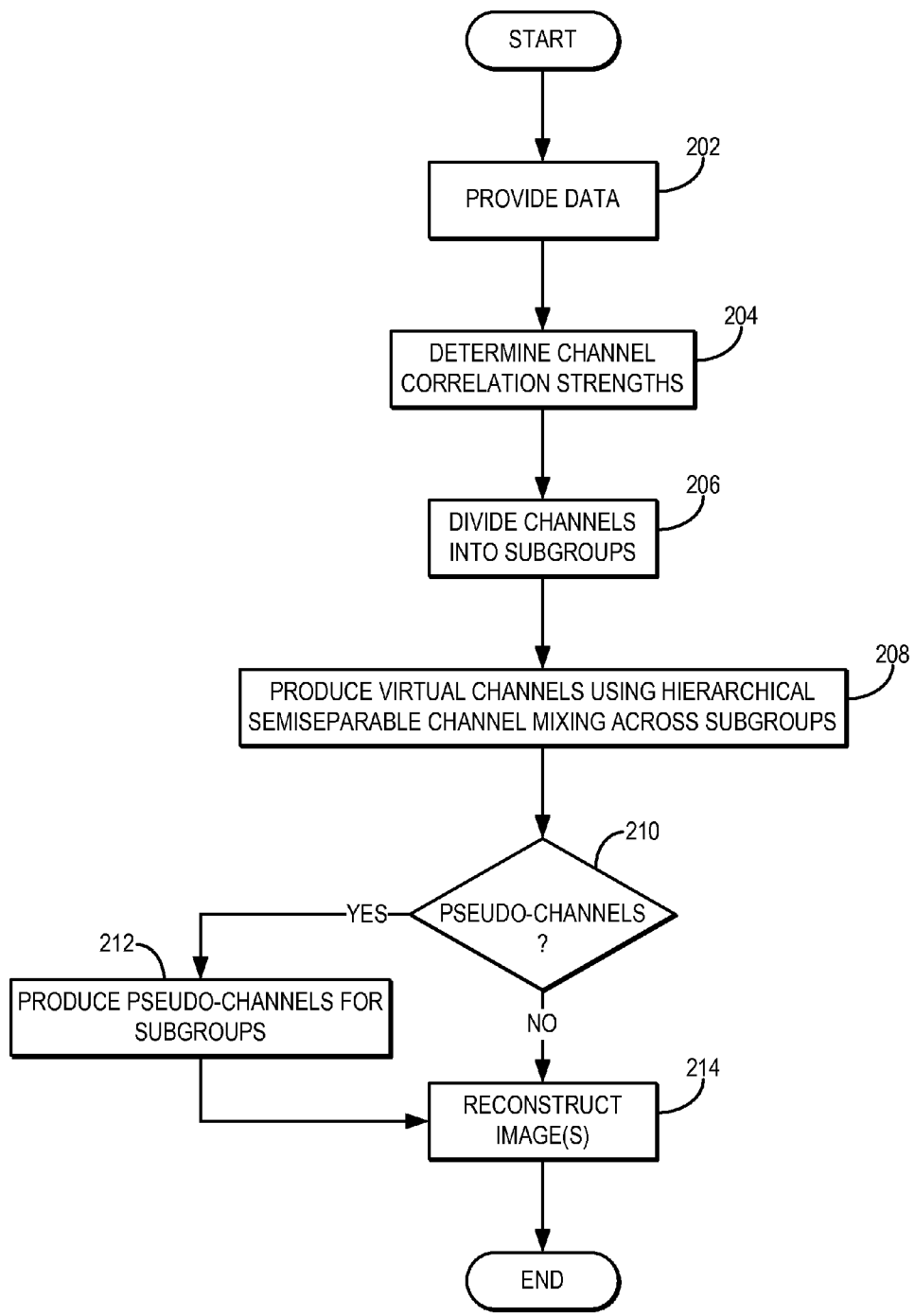
FIG. 2 is a flowchart setting forth an example method for reconstructing an image of a subject using an HMF-based coil compression.

Referring now to FIG. 2, a flowchart setting forth the steps of an example method for reconstructing an image from highly-accelerated data using an HMF-based coil compression is illustrated. The method begins by providing data that has been acquired with an MRI system, as indicated at step 202. In some embodiments, the data has been previously acquired and can thus be provided by retrieving the previously acquired data from storage. In other embodiments, the data can be provided by acquiring it from a subject with an MRI system. Preferably, the provided data is acquired using an accelerated data acquisition scheme. Examples of accelerated acquisitions include undersampling k-space, performing a simultaneous multislice acquisition, or both.

To implement the HMF method, the strength of correlation of each coil in the receive coil array is determined, as indicated at step 204. This strength of correlation is then used to divide the receive channels into a plurality of different subgroups, as indicated at step 206. After the channels have been assigned to different subgroups, a set of virtual channels is formed for each subgroup, as indicated at step 208. For instance, a hierarchically semiseparable channel mixing can be implemented to form the virtual channels. Advantageously, the HMF-based coil compression can be interfaced with existing Cartesian and non-Cartesian optimized compression schemes.

Optionally, pseudo-channels can be produced for each subgroup, thereby further reducing the number of effective channels, as will be described below in more detail. If pseudo-channels are desired, as determined at decision block 210, then they are produced as indicated at step 212. Using the subgroups of reduced channels, one or more images can be reconstructed from the provided data, as indicated at step 214. Any suitable parallel image reconstruction method can be used. For instance, the HMF-based coil compression described here can be directly used for GRAPPA and slice-GRAPPA based reconstructions. In general, the reconstruction includes reconstructing an image for each subgroup and then combining the subgroups images to produce the final image.

PI reconstruction methods such as GRAPPA and Sp-SG are formulated to use all available channels as part of the unaliasing of accelerated data. For example, in the simple eight channel geometry of FIG. 1, both methods will employ all of the channels in the full set 102 to unalias any one given channel, $C_n$. Typically, compression methods rely on a global mapping framework ("GMF") that maps the original channels to a subset of channels to reduce the PI problem size.

The HMF-based coil compression can be used to create a hierarchical grouping of the channels with smaller associated distinct PI systems to solve. For example, as illustrated in FIG. 1, an eight channel geometry can partition the original channels into four subgroups of channels that are strongly correlated to one another. In this example, two virtual coils are generated for each subgroup from the other six original channels (e.g., using SVD or GCC). A PI problem is solved for each subgroup in order to estimate unaliased images for the two original channels assigned to that subgroup. To improve efficiency, a pseudo-channel can also be solved for, where the pseudo-channel has a magnitude that is the sum-of-squares combination of the two original channels in the subgroup.

The additional flexibility provided by HMF enables alternative coil compression techniques to be used for many acquisition types. In the case of Cartesian sampling, HMF can be used to bring the level of performance for SVD compression sustainably closer to that observed with the Cartesian-optimized GCC compression. Because HMF exploits the coil array topology through correlation, the benefits should extend to irregular sampling patterns and coil geometries.

Figure 3:
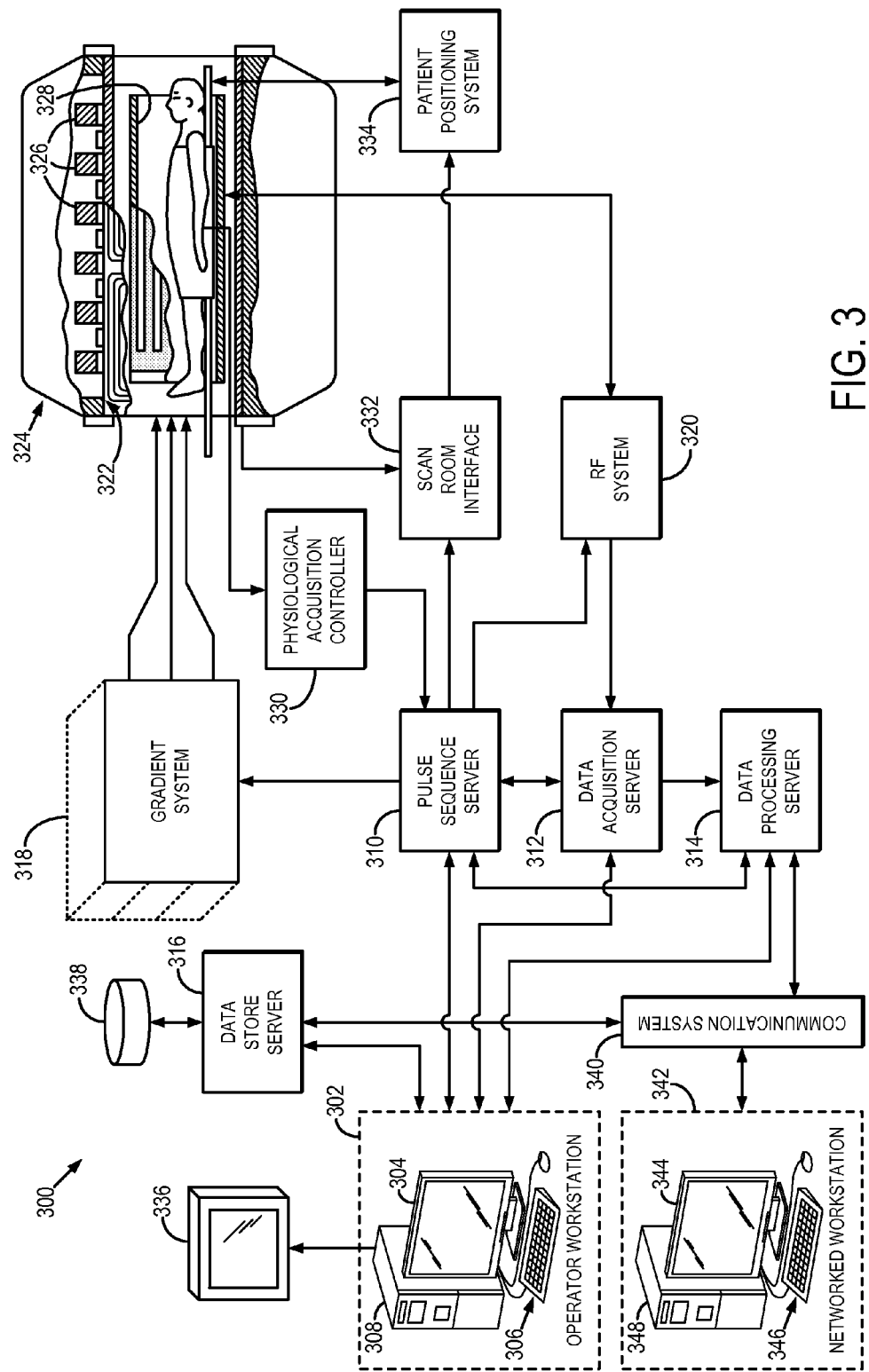
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing an image of a subject using a magnetic resonance imaging (MRI) system, the steps of the method comprising:
    (a) acquiring data from a subject using the MRI system, wherein the data is acquired using a plurality of receive channels associated with a radio frequency (RF) coil array;
    (b) determining a strength of correlation between the plurality of receive channels;
    (c) creating subgroups of the receive channels based on the determined strength of correlation between the plurality of receive channels;
    (d) producing at least one virtual channel for each subgroup using a hierarchical semiseparable channel mixing across the subgroups;
    (e) reconstructing an image for each subgroup from the acquired data and using the receive channels and virtual channels in each respective subgroup; and
    (f) producing an image of the subject by combining the reconstructed images for each subgroup.

2. The method as recited in claim 1, wherein step (c) includes creating the subgroups such that each subgroup contains at least two of the plurality of receive channels, wherein the at least two receive channels are more strongly correlated to each other than other receive channels.

3. The method as recited in claim 1, wherein step (d) includes producing the at least one virtual channel using a coil compression algorithm subject to the hierarchical semiseparable channel mixing.

4. The method as recited in claim 3, wherein the coil compression algorithm is a singular value decomposition-based coil compression algorithm.

5. The method as recited in claim 3, wherein the coil compression algorithm is a geometric-decomposition coil compression algorithm.

6. The method as recited in claim 3, wherein the coil compression algorithm uses a global mapping framework to produce a virtual coil for a particular subgroup by compressing channels not in the particular subgroup into the virtual coil.

7. The method as recited in claim 1, wherein step (c) further includes producing at least one pseudo-channel for a particular subgroup based on the receive channels selected to be in that particular subgroup.

8. The method as recited in claim 7, wherein producing the at least one pseudo-channel includes solving a non-linear least squares problem to compute a magnitude of the at least one pseudo-channel as a sum-of-squares combination of the receive channels in the particular subgroup.

* * * * *

UNITED STATES PATENT AND TRADEMARK OFFICE
CERTIFICATE OF CORRECTION

PATENT NO. : 10,310,042 B2  
APPLICATION NO. : 15/305436  
DATED : June 4, 2019  
INVENTOR(S) : Stephen Cauley et al.

Page 1 of 1

It is certified that error appears in the above-identified patent and that said Letters Patent is hereby corrected as shown below:

On the Title Page

Item (54) and in the Specification, Column 1 Line 1 Title, "HIERRARCHICAL" should be --HIERARCHICAL--.

Signed and Sealed this  
Sixth Day of August, 2019

Andrei Iancu  
*Director of the United States Patent and Trademark Office*